United States Patent
Goroszeniuk

(10) Patent No.: US 7,613,517 B2
(45) Date of Patent: Nov. 3, 2009

(54) METHOD FOR NEUROSTIMULATION

(76) Inventor: Teodor Goroszeniuk, 15a Abbotsbury Road, London W14 SES (GB)

( * ) Notice: Subject to any disclaimer, the term of this patent is extended or adjusted under 35 U.S.C. 154(b) by 0 days.

(21) Appl. No.: 11/219,803

(22) Filed: Sep. 7, 2005

(65) Prior Publication Data
US 2006/0052834 A1  Mar. 9, 2006

(30) Foreign Application Priority Data
Oct. 20, 2004 (GB) ................................. 0423313.6
Mar. 18, 2005 (GB) ................................. 0505643.7

(51) Int. Cl.
*A61N 1/34* (2006.01)
(52) U.S. Cl. ........................................ 607/46; 607/150
(58) Field of Classification Search ............. 607/46–47, 607/150, 149
See application file for complete search history.

(56) References Cited

U.S. PATENT DOCUMENTS

| | | | | |
|---|---|---|---|---|
| 4,232,680 A | * | 11/1980 | Hudleson et al. | 607/46 |
| 4,509,521 A | * | 4/1985 | Barry | 607/46 |
| 4,541,432 A | * | 9/1985 | Molina-Negro et al. | 607/46 |
| 4,580,570 A | * | 4/1986 | Sarrell et al. | 607/63 |
| 4,633,888 A | * | 1/1987 | Yoneyama | 607/149 |
| 4,962,766 A | * | 10/1990 | Herzon | 600/554 |
| 5,117,826 A | * | 6/1992 | Bartelt et al. | 607/46 |
| 5,205,297 A | * | 4/1993 | Montecalvo et al. | 607/152 |
| 5,674,261 A | * | 10/1997 | Smith | 607/46 |
| 6,010,467 A | * | 1/2000 | Smith | 601/15 |
| 6,309,407 B1 | * | 10/2001 | Frankie | 607/46 |

* cited by examiner

*Primary Examiner*—Mark W Bockelman
(74) *Attorney, Agent, or Firm*—Dennison, Schultz & MacDonald

(57) ABSTRACT

The invention relates to a device for treating a patient for neurological or muscular pain by neurostimulation comprising a pair of electrodes to be applied externally, ie. to the surface of the skin, in the region of the pain and to apply a current of between 0.2 and 12 mA at a frequency of between 1 and 50 Hz, and preferably between 2 and 10 Hz. Optimal results appear to be achieved when the applied current is between 3 and 10 mA. In use at least one of the electrodes, a stimulating electrode is used to accurately locate the pain and during treatment the electrode is applied to the patient's skin as located using mild pressure, while a stimulating pulse is applied as treatment. This action produces a remarkable and unexpected level of pain relief. The invention extends to a method for the treatment of neurological pain using the above parameters and procedure.

5 Claims, 5 Drawing Sheets

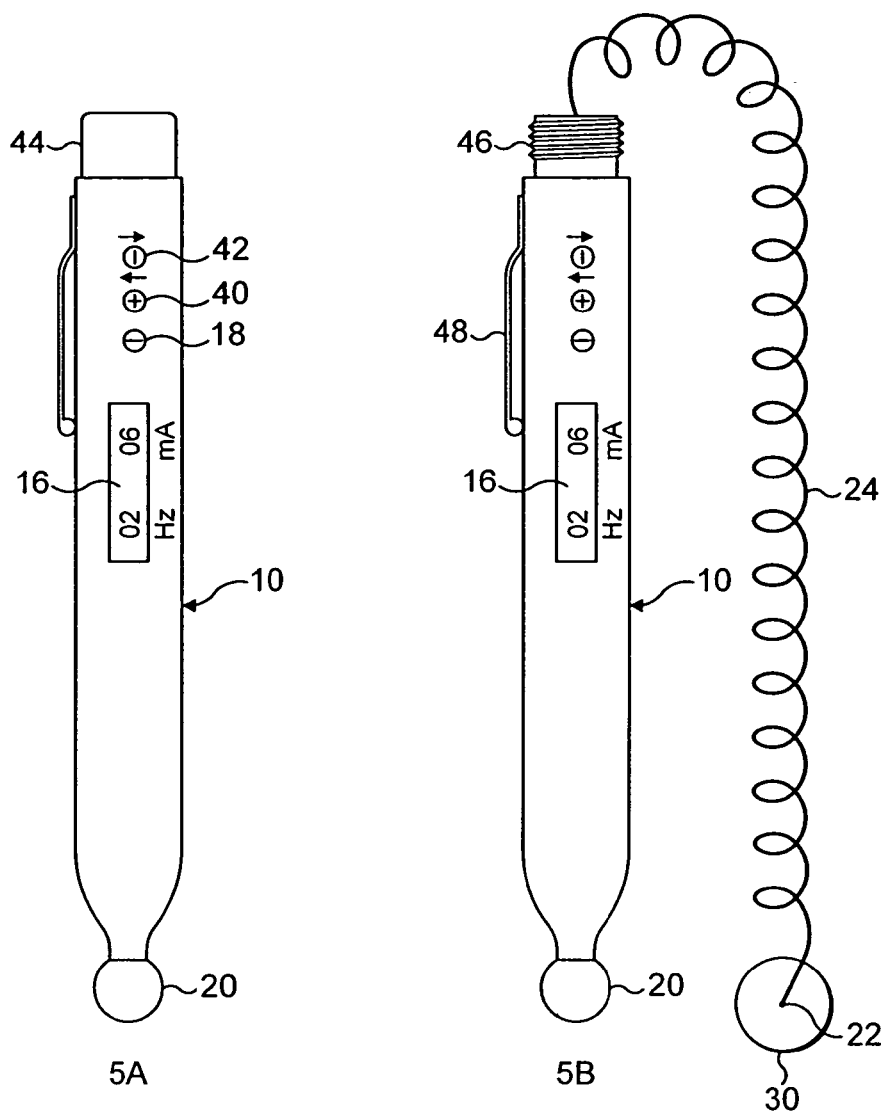
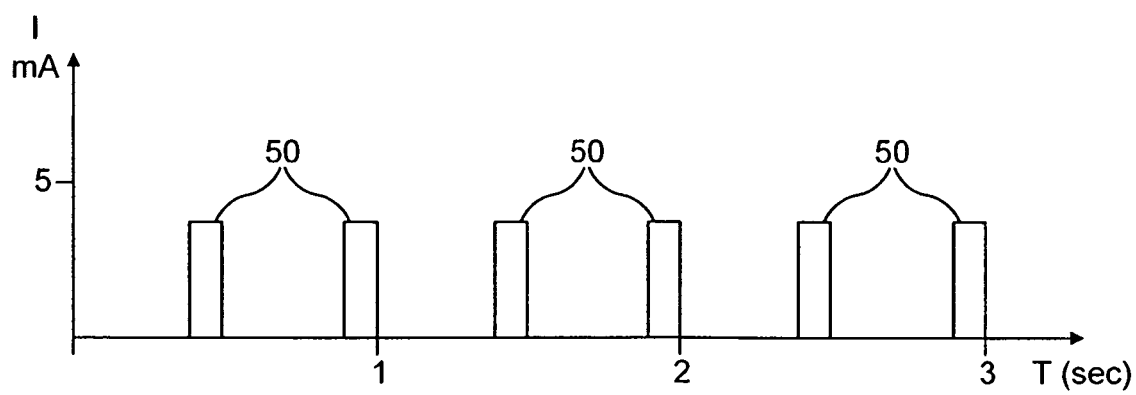
FIG. 5
FIG. 6

METHOD FOR NEUROSTIMULATION

BACKGROUND OF THE INVENTION

This invention relates to improvements in neurostimulation for the treatment of chronic pain.

Neurostimulation is gaining in popularity as a treatment of chronic pain. Traditionally such neurostimulation has relied on the implantation of a device in a position adjacent to an affected area. An electrical stimulation is applied to implanted electrodes to achieve a level of relief in the patient. However, such devices need to be accurately located and generally require a small surgical procedure in order to implant the device. The procedure is carried out by a trained medical practitioner or specialist.

SUMMARY OF THE INVENTION

In accordance with the invention a device for the treatment of neurological or muscular pain by electrical neurostimulation comprises a pair of electrodes and an electronic power supply arranged to supply a pulsed signal between the electrodes of which one electrode is a reference electrode for attachment to the skin of a patient, and the other electrode is a stimulating electrode preferably comprising a rigid stem with a substantially rounded end which is arranged, in use, to be pressed firmly onto a patient's skin both to accurately locate the source of pain in response to a locating pulse and then to remain in place as located to treat the pain by applying an appropriate stimulating pulsed signal transcutaneously to treat the pain.

The fact that the electrodes are applied externally for non-invasive use permits the device to be used and, to a certain extent, controlled by a patient, although its initial set-up will be performed by a medical practitioner or specialist. The very low current which has been found to be effective allows the device to be manipulated safely by older people—the most frequent sufferers from chronic pain—or even by children or people who are handicapped.

The present invention must be distinguished from the known transcutaneous electrical nerve stimulation (TENS) in which silicon-rubber/carbon electrodes are stuck onto a patient's skin in the region of an affected or painful area. In the present invention, a stimulating electrode is arranged to be accurately located with respect to an affected nerve. In addition the stimulating electrode has a rigid, rounded end, generally at the end of a rigid stem, which can be 1) applied firmly to the skin in the affected area as located either by the device in a location mode or by a separate nerve locator, 2) moved in response to the patient's reaction to the stimulating signal applied to the stimulating electrode further to fine-tune the treatment, and 3) remain in the selected position as located in steps 1) and 2) above to treat the pain as long as may be required.

Once the stimulating electrode has been accurately located the current can be reduced in most cases and the frequency can be adjusted to produce the optimum level of relief. Accurate location of the electrode thus reduces the discomfort to the patient and the risk of burning. It also prolongs battery life for a portable device.

The energy required for the treatment may depend on the size of the nerves (large, heavily myelinated A motor fibres at one extreme versus smaller unmyelinated C fibres at the other). Thus the energy delivered E (energy in nC)=I (current in mA)×t (duration in s). In order to obtain the necessary transcutaneous current a relatively high voltage—up to 85V, though more traditionally 65V—may be required. The pressure that can be applied by the stimulating electrode (and by the other, reference, electrode) to the skin allows the voltage to be reduced because of the lower resistance, making burning less likely. The rounded end of the electrode(s) also act to distribute the current more accurately and evenly than would be achieved by a traditional silicon carbon electrode.

Whilst formerly the treatment was set by adjusting the voltage, it is usual today to set the stimulating current, and the device automatically adjusts the voltage as required irrespective of the impedance.

The treatment is found to be effective in most cases in about five minutes, though it may be applied for less time or for longer according to the symptoms and level of relief achieved.

One of the most important components of this novel approach to peripheral neuromodulation in treatment of neuropathic pain is the frequency of the stimulation, which is contrary to established recommendations. The frequency is particularly effective in the slow range of stimulation 2-10 Hz, but can occasionally be successful at higher levels 10-50 Hz, but not usually in the 50-150 Hz range.

This external approach whereby the electrical impulse is applied externally over the nerves, plexuses and at non-specific areas in a non-segmental distribution produces results which are overwhelming. Pain relief can be compared to the percutaneous direct approach, with results of the same magnitude of 70-100% pain relief achieved as measured on a VAS score.

The duration of the pain relief following a typical 5 min session where the electrodes have been placed correctly can vary between minutes or hours and days or even weeks.

Since the cathodic (negative) threshold current is likely to be 3 to 5 times lower than the anodic threshold current, it is generally preferred to use the cathode as the stimulating electrode.

The device is most effective when the stimulating electrode comprises a substantially hemispherical contact which projects in such a way that they can be applied to an affected area with sufficient pressure that it produces a small indentation in the skin. In one embodiment, one or both of the electrodes are mounted on a semi-rigid support or supports having straps or other means which when in use enable each contact to be pressed firmly against a patient's skin in the affected region.

In other embodiments one of the electrodes, the reference electrode, comprises a silicon-carbon patch connected to the power supply and is arranged to be stuck to the skin close to the affected area. A gel may be used to enhance the conductivity between the reference electrode and the skin. The other electrode, the stimulating electrode, comprises a short rod or stem whose contact end is rounded or is provided with a small ball which is applied to a patient as described above. The stimulating electrode may either be rigidly attached (screwed in or permanently fixed, for example) to the power supply, or attached to it by a wire as mentioned above.

This combination of pressure together with the electrical stimulation provides a surprising level of relief comparable to that achieved by a percutaneous implant. In a recent trial, in more than half the patients on which the device was used the VAS pain score was reduced to 0 over a period of five minutes.

For maximum effectiveness the electrodes are accurately positioned using the device in its stimulator and location mode prior to treatment. Thus, the device is first used to position the treatment electrodes prior to fine-tuning the treatment current and frequency. The power supply may then be adjusted and used to provide the desired electrical output to the electrodes for the treatment.

As it may not be necessary to carry out the location procedure on each occasion, either a separate nerve stimulator may be used by a specialist practitioner, or the location function may be switched off so that the patient is not confused. The treatment parameters equally may be pre set or pre-limited to prevent the patient from harming himself by mistake.

The diameter of the contacts of the electrodes will depend on the muscle or nerve type to be treated. They may be between 1 and 12 mm or in some cases up to 20 mm, but generally 3 to 6 mm. They may be mounted on the inner side (in use) of a semi-rigid strap which may be attached to a patient by means of a sticky plaster or strip of Velcro (® 3M Corp. Inc.).

As electronic devices become ever smaller and more compact, one embodiment of the device may be in the form of a pen. The stimulating electrode is located at the 'writing end' whilst the reference electrode is stored at the other end of the 'pen' and is arranged to be connected to the patient by means of a plaster or a patch. A gel may be required to improve the conductivity between the reference electrode and the skin.

The invention extends to a method of treating a patient for neurological or muscular pain by neurostimulation comprising applying a pair of electrodes externally, ie. to the surface of the skin, in the region of the pain and locating the stimulating electrode accurately prior to applying a stimulating pulse of between 0.2 and 12 mA at a frequency of between 1 and 50 Hz, and preferably between 2 and 10 Hz. Optimal results appear to be achieved when the applied current is between 3 and 10 mA. As mentioned above, the electrodes are applied to the patient's skin using mild but firm pressure which causes them to produce an indentation in the skin. This action appears to enhance the success of the treatment and indeed makes effective nerve stimulation possible by means only of externally-positioned electrodes.

External neurostimulation in accordance with the invention results in improved relief of chronic neuropathic pain, an improvement in peripheral circulation, improved mobility and improved sensory perception, comparable with the results achieved by percutaneous treatment. It has the great advantage that it can be applied by the patient him/herself when required and as often as they wish with little or no adverse effects. As no surgical procedure is required, treatment can be easily be modified or stopped if it fails to produce the desired relief or if it causes an unwelcome response.

Additionally, it can be used in conjunction with traditional implants either to complement the relief or if the site of the pain moves. This is particularly useful in the treatment of non-specific or non-segmental pain.

BRIEF DESCRIPTION OF THE DRAWINGS

The invention will now be further described by way of example with reference to the accompanying drawing in which:

FIG. 5 is a diagrammatic view of a device in accordance with the invention in the form of a pen. 5A shows the device as stored, and 5B shows it ready for use, and FIG. 6 shows a typical wave form of a stimulating signal.

DESCRIPTION OF THE PREFERRED EMBODIMENTS

Figure 1:
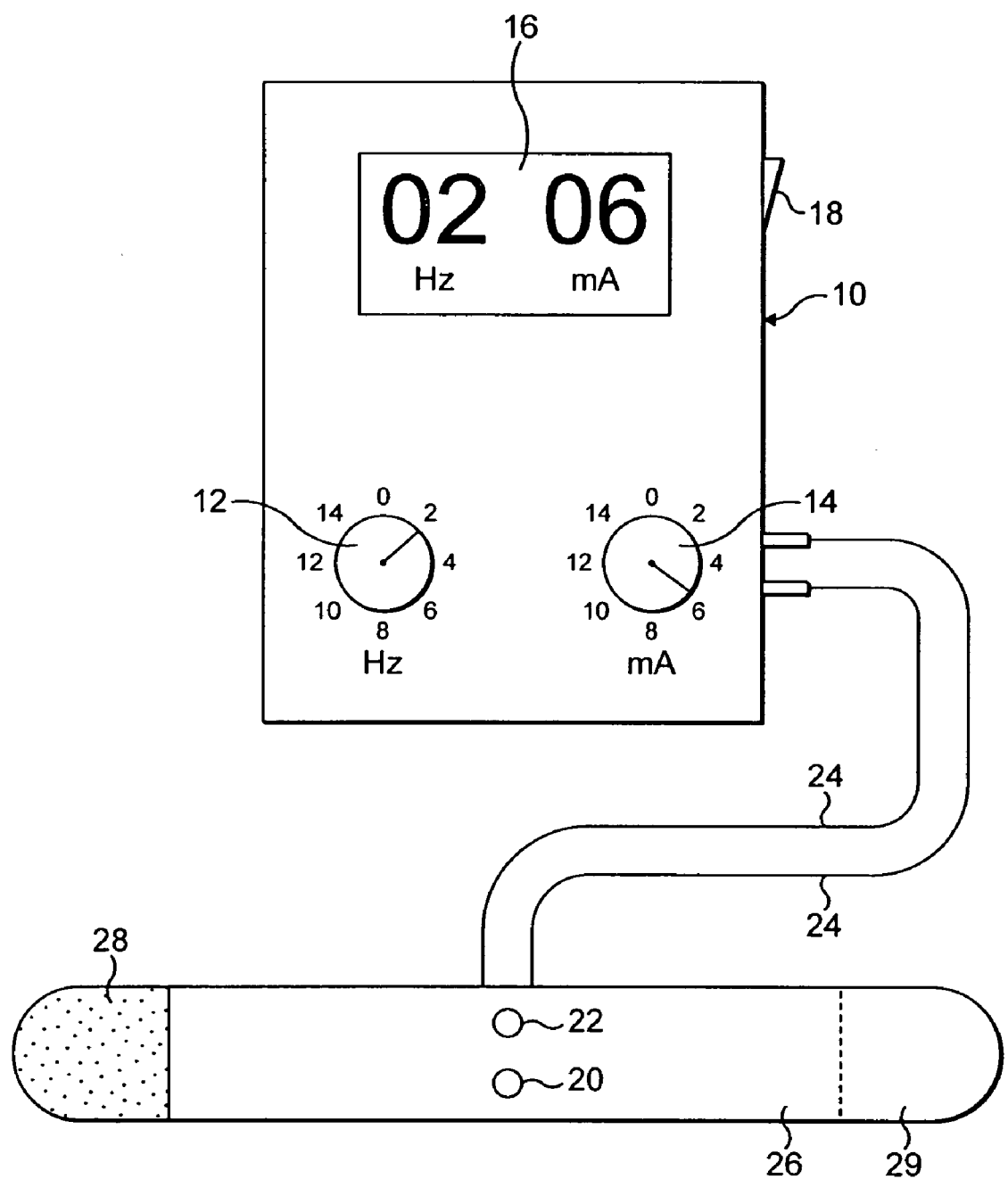
FIG. 1 is a diagrammatic view of a device in accordance with the invention.

In FIG. 1 the device comprises a control unit which incorporates a power supply 10 which is controlled by a frequency button 12 and a power button 14. The output parameters are displayed on an LCD screen 16. An on/off switch is provided at 18.

The output from the device is supplied to two electrodes 20,22 by leads 24. The electrodes 20,22 each comprise a substantially hemispherical projection protruding from a semi-rigid strap 26. The strap shown is for attaching around a patient's wrist and has a length of Velcro® 28 at one end which attaches to a corresponding patch 29 on the other side of the strap.

The electrodes each have a diameter of 4 mm and project 8 to 10 mm from the strap. They are held firmly on the strap so that when the latter is attached, for example, around a patient's wrist, they cause an indentation in the patient's flesh. They are spaced apart by about 20 to 30 mm in most cases, though they may be adjustable as the exact required spacing will depend upon the diagnosis and the treatment required. In practice one of the electrodes acts to produce a contact with the patient's skin as a reference electrode 22 whilst the other, or stimulating electrode 20, is positioned in respect of the point in the affected area, which produces the optimum level of relief.

Figure 2:
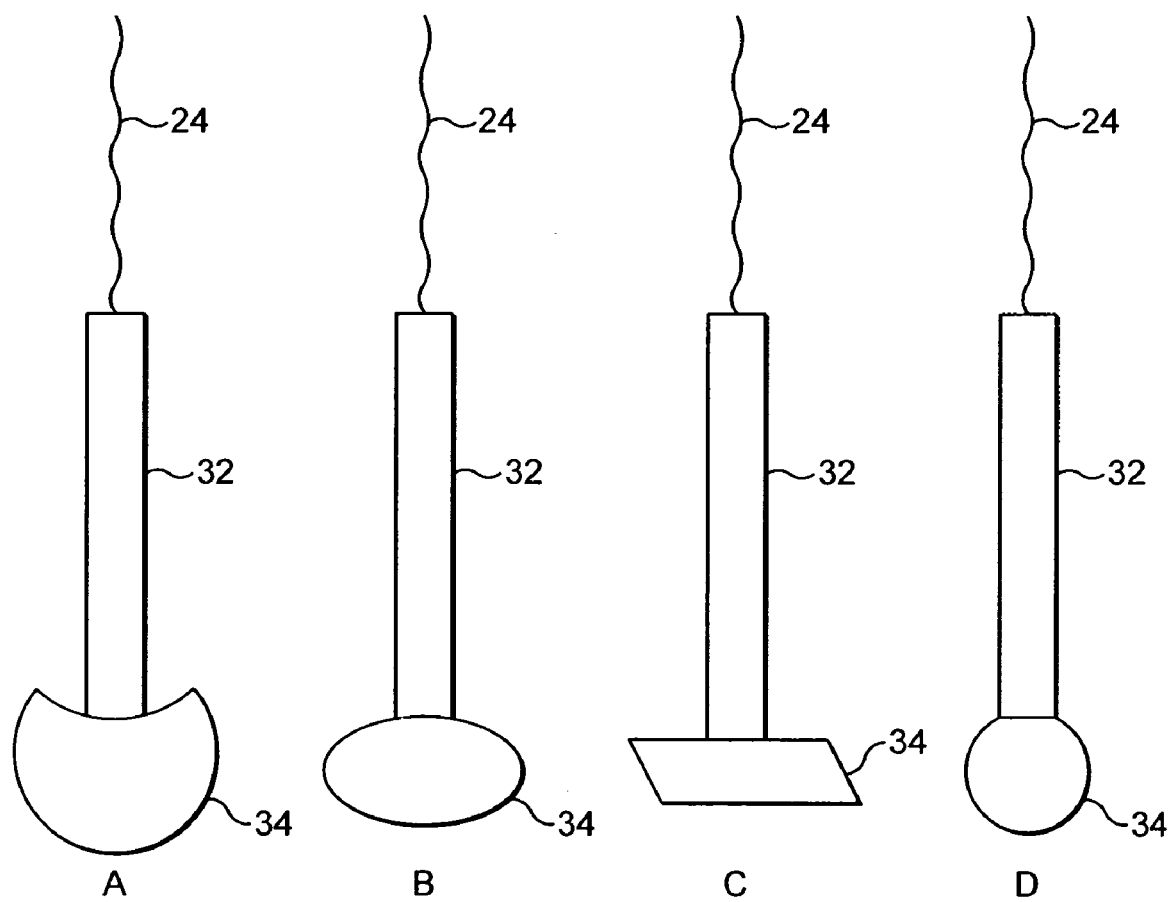
FIG. 2 is a diagrammatic side elevation of several electrode forms suitable for use with the device.

FIG. 2 shows elevations of several electrode forms suitable for use with the device. The electrode in FIG. 2A has a stem 32 connected to a lead 24 from the power supply 10, and a rounded contact end 34 substantially in the form of a sphere. This electrode form is used for larger sites and may measure up to about 20 mm in diameter. It may be used with the higher currents prescribed.

FIG. 2B shows a flat elliptical electrode measuring up to 10 mm by 20 mm for use as the electrode in FIG. 2A. FIG. 2C shows a rectangular electrode for applications similar to those for which that in FIG. 2B is used.

FIG. 2D shows the preferred spherical electrode whose spherical contact end 34 is about 5 to 6 mm in diameter. This electrode appears to produce good results in the majority of cases. However for specific applications it may be smaller, down to 1 mm, or indeed larger as required.

Whilst a pair of similar electrodes may be used, a practitioner may decide that two dissimilar electrodes may produce a better response for a specific condition or may attach a reference electrode to the patient by means of a patch whilst using a solid metal electrode as shown in FIG. 2 for the stimulating electrode in order to be able to apply it sufficiently firmly to the patient's skin to achieve an improved level of relief.

Figure 3:
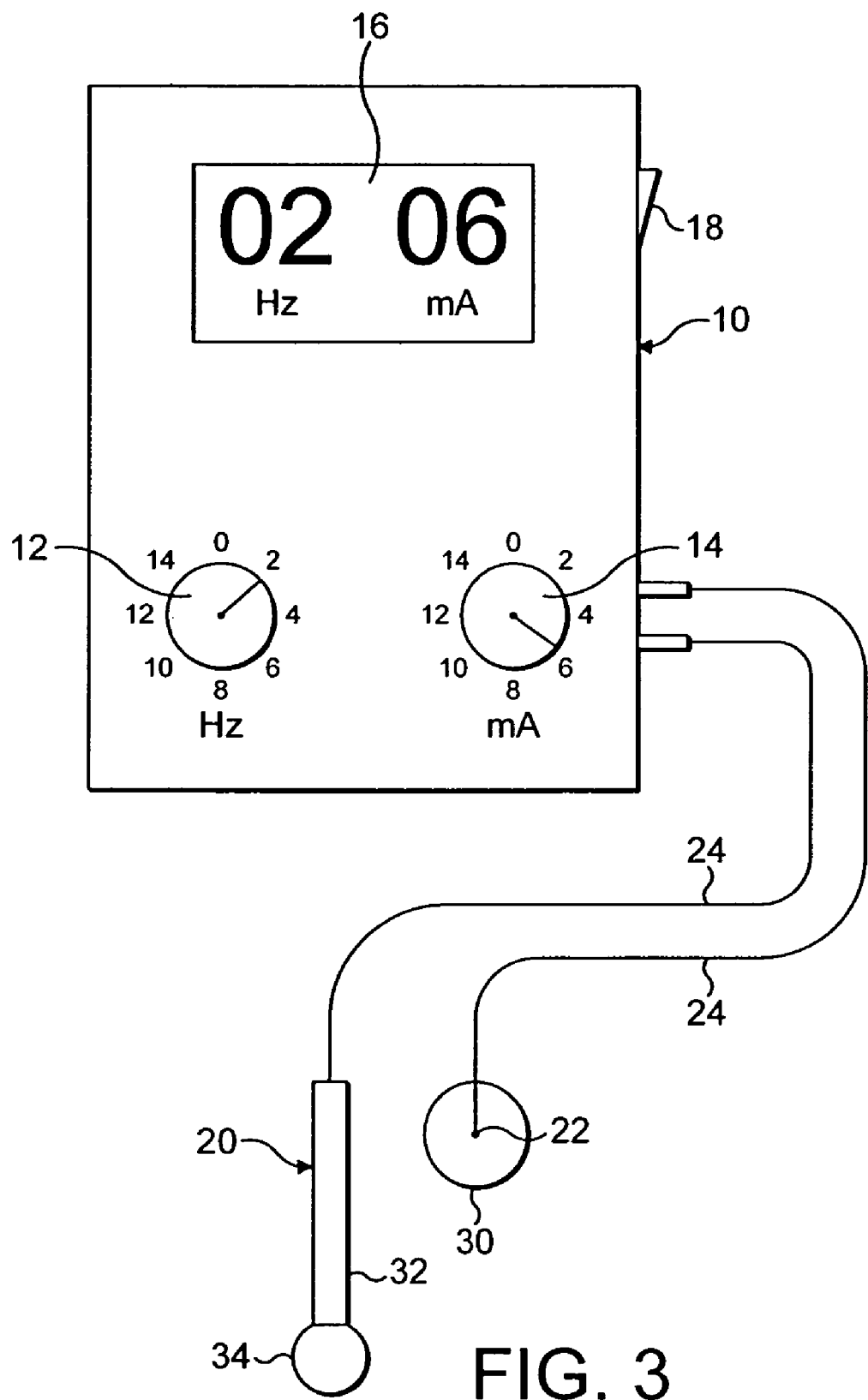
FIG. 3 is a diagrammatic view of a device in accordance with the invention, similar to that shown in FIG. 1.

In FIG. 3 the device is similar to that in FIG. 1 but that the reference electrode 22 comprises a silicon-carbon patch 30 connected to the power supply 10 and arranged to be attached to the skin close to the affected area. A gel may be used to enhance the conductivity between the reference electrode and the skin. The other electrode, the stimulating electrode 20, comprises a short stem 32 whose contact end 34 is rounded or has a small ball formed at its end, or indeed any suitable form shown or described above in FIG. 2. In use a stimulating pulse is applied to the stimulating electrode to find an accurate location of the affected nerve. Once this has been correctly located, the electrode is applied firmly to the patient's skin whilst the stimulating signal is adjusted to provide the optimum level of relief without minimising any discomfort.

Figure 4:
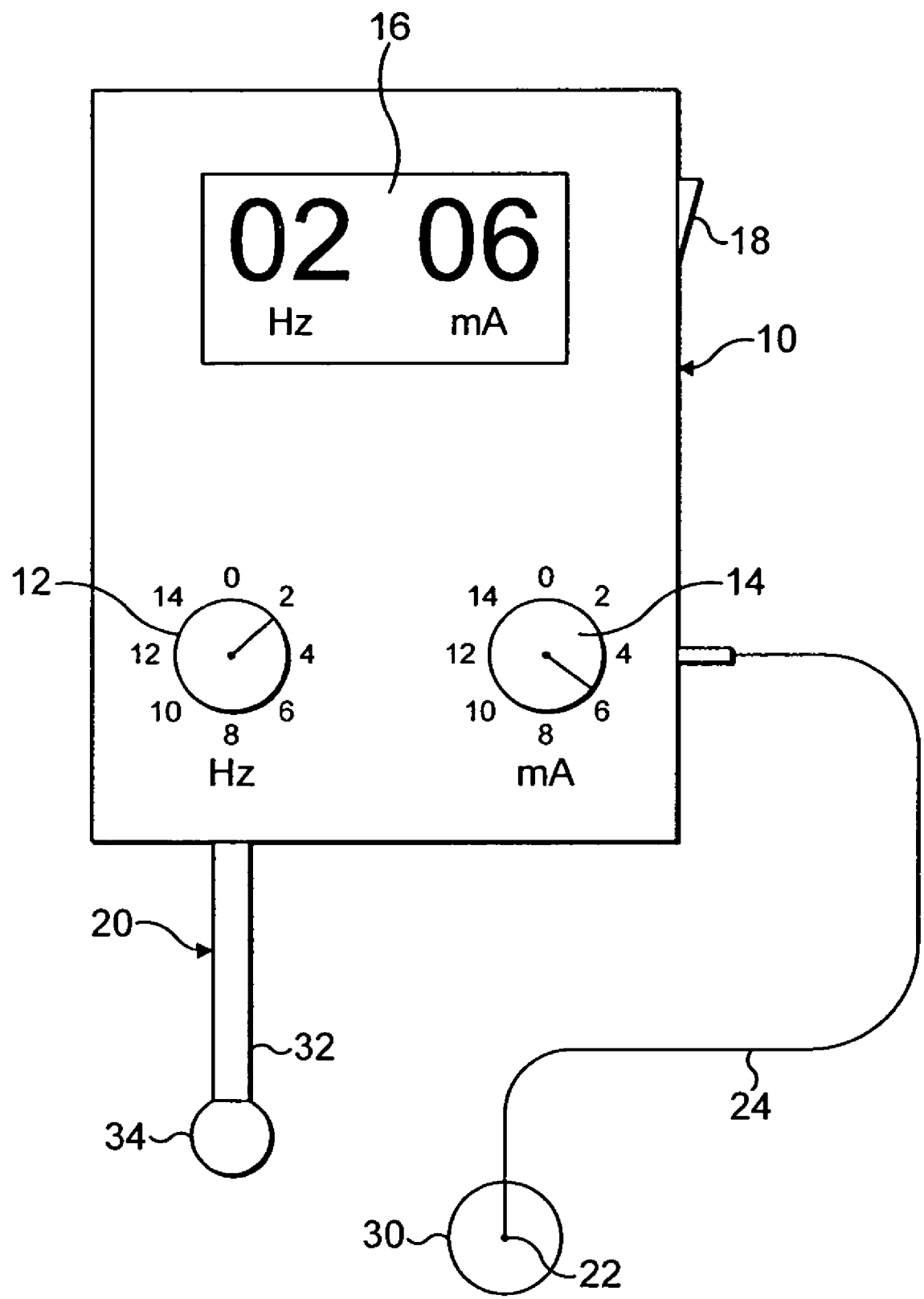
FIG. 4 is a diagrammatic view of a device in accordance with the invention, similar to that shown in FIG. 3.

FIG. 4 shows a device similar to that in FIG. 3, but that the stimulating electrode 20 is rigidly attached for use by being screwed or clipped into the power supply 10, Alternatively it may be permanently fixed to it. In all other respects it is similar to that shown in FIG. 3. The stimulating electrode must however be sufficiently stiff and suitably dimensioned that it can be applied firmly to a patient to produce a good electrical and physical contact with the skin.

FIG. 5 shows a stimulating device in the form of a pen whose body houses the power supply 10 and the necessary controls (on/off and function buttons), increase button 40, decrease button 42 and an LCD screen 16. A stimulating electrode 20 in the form of a small ball is provided at the 'writing end' whilst a reference electrode 22 is stored at the other end of the 'pen' under a screw cap 44 (FIG. 5A) and screw thread 46 (5B). In use, as shown in 5B, a reference electrode 22 is withdrawn from the upper end of the 'pen' and extended so that it can be attached to the skin of a patient by means of a plaster 30 as above. The 'pen' may be clipped into a patient's pocket, ready for use, by means of a clip 48.

Other forms of the device are possible. For example, many sufferers of acute pain have muscular or other disabilities which make it difficult for them to hold the device in a way that applies the appropriate pressure in the desired location. In such cases it may be appropriate to provide a 'pistol' grip with the electrode, for example, at the end of the barrel.

Since the cathodic (negative) threshold current is likely to be 3 to 5 times lower than the anodic threshold current, it is generally preferred to use the cathode as the stimulating electrode, in other words, making it the negative.

In use, the combination of the pressure and the, albeit small, stimulating current appears to have a remarkably beneficial effect in terms of the pain relief achieved.

The power button 14 of the power supply is adjustable to provide a current of 0.2 mA to 12 mA at a frequency that can be varied by the frequency button 12 from 2 to 10 Hz. It has been found that for many patients the optimum stimulation occurs at a frequency of 2 to 3 Hz and a current of between 3 and 10 mA with a pulse duration of between, say, 10% and 50%. An example of the stimulating pulse is shown in FIG. 6. In this case a square-wave with a frequency of 2 Hz has a pulse duration of 10% of the wave length. This appears to produce an effective treatment whilst enhancing battery life in the case of a portable device. The duration of the pulse may vary from about 5% to 60% of the wavelength whilst remaining effective for the treatment. The shorter the pulse and the lower the current the longer the battery life in the case of a portable device.

In a trial, a device in accordance with the invention was used to treat patients with the following pain presentations: CRPS with scar areas on the pelvis, testes, abdomen, chest wall, neck, breast, as well as for phantom limbs and chest pain. The following Table summarises the results of the treatment

| Patients | % pain relief VAS score |
| --- | --- |
| 17 | 100 |
| 4 | 90 |
| 8 | 50-90 |
| 3 | <50 |

Whilst such effective treatment would in all probability have been achieved using an implanted device, the success of this non-invasive, external treatment is astonishing. The flexibility and convenience of external stimulation is thus greatly appreciated by patients and specialists alike.

The invention claimed is:

1. A method for locating and treating chronic or acute pain in a patient, comprising the steps of:

accurately locating an affected nerve of a patient by placing on the skin of the patient a reference electrode in the form of a removable patch, then pressing against the skin of the patient a substantially rounded stimulating electrode of diameter of about 3 to 12 mm, at an end of a rigid stem, and applying between the reference and stimulating electrodes an electrical current;

moving the stimulating electrode to points on the skin to locate an affected, pain-causing nerve based on the reaction of the patient;

applying pressure to the stimulating electrode against the affected nerve simultaneously with applying between the reference and stimulating electrodes stimulating electrical pulses of frequency 1 to 10 Hz, and current between 0.2 and 12 ma;

varying frequency and current of the pulses to optimize pain relief, and maintaining pressure against the affected nerve for a time sufficient to achieve relief of the pain.

2. A method as claimed in claim 1, wherein the applied frequency is between 2 and 3 Hz.

3. A method as claimed in claim 2, wherein the applied current is between 3 and 10 mA.

4. A method as claimed in any of claim 2, wherein the stimulating pulse is applied for 5 minutes.

5. A method as claimed in claim 2, wherein a negative current is applied to the stimulating electrode.

* * * * *